United States Patent [19]

Bodor

[11] Patent Number: 4,824,676
[45] Date of Patent: Apr. 25, 1989

[54] PHYSIOLOGICAL MEANS OF ENHANCING TRANSDERMAL DELIVERY OF DRUGS

[75] Inventor: Nicholas Bodor, Gainesville, Fla.

[73] Assignee: Schering Corporation, Kenilworth, N.J.

[21] Appl. No.: 14,317

[22] Filed: Feb. 13, 1987

Related U.S. Application Data

[63] Continuation-in-part of Ser. No. 659,919, Oct. 11, 1984, abandoned.

[51] Int. Cl.$^4$ .................... A61F 13/00; A61K 7/32
[52] U.S. Cl. ...................................... 424/449; 424/65; 424/443; 424/447
[58] Field of Search .................. 424/443, 65, 449, 447

[56] References Cited

U.S. PATENT DOCUMENTS

| | | | |
|---|---|---|---|
| 3,312,709 | 4/1967 | MacMillan | 424/65 |
| 3,326,768 | 6/1967 | MacMillan | 424/65 |
| 3,624,200 | 11/1971 | Moffett | 424/65 |
| 3,742,951 | 7/1973 | Zaffaroni | 424/28 |
| 3,767,786 | 10/1973 | MacMillan | 424/65 |
| 3,775,538 | 11/1973 | DeSalva et al. | 424/65 |
| 3,921,636 | 11/1975 | Zaffaroni | 128/260 |
| 3,943,242 | 3/1976 | Fogel et al. | 424/65 |
| 3,953,599 | 4/1976 | MacMillan et al. | 424/65 |
| 3,989,816 | 11/1976 | Rajadhyaksha | 424/60 |
| 4,031,894 | 6/1977 | Urquhart et al. | 604/897 |
| 4,060,084 | 11/1977 | Chandrasekaran et al. | 604/897 |
| 4,291,015 | 9/1981 | Keith et al. | 424/28 |
| 4,292,302 | 9/1981 | Keith et al. | 424/28 |
| 4,292,303 | 9/1981 | Keith et al. | 424/28 |
| 4,294,820 | 10/1981 | Keith et al. | 424/28 |
| 4,311,481 | 1/1982 | Nelson | 8/564 |
| 4,316,893 | 2/1982 | Rajadhyaksha | 424/180 |
| 4,390,520 | 6/1983 | Nagai et al. | 424/28 |
| 4,409,206 | 10/1983 | Stricker | 424/81 |
| 4,440,777 | 4/1984 | Zupan | 514/785 |
| 4,466,953 | 8/1984 | Keith et al. | 424/28 |
| 4,483,846 | 11/1984 | Koide et al. | 424/28 |
| 4,540,564 | 9/1985 | Bodor | 514/176 |
| 4,559,222 | 12/1985 | Enscore et al. | 424/28 |
| 4,560,553 | 12/1985 | Zupan | 424/78 |
| 4,675,178 | 6/1987 | Klein et al. | 424/65 |
| 4,724,240 | 2/1988 | Abrutyn | 424/65 |
| 4,741,899 | 5/1988 | Henry et al. | 424/47 |

FOREIGN PATENT DOCUMENTS 2010270 6/1979 United Kingdom.

*Primary Examiner*—Thurman K. Page
*Attorney, Agent, or Firm*—Anita W. Magatti; James R. Nelson; Stephen T. Miller

[57] ABSTRACT

A method of enhancing transdermal delivery of a pharmaceutically active drug from a transdermal delivery system as well as a transdermal delivery system capable of providing a desirable flow interface between the delivery system and the skin surface are disclosed. The method involves pre-treating an area of skin with an anticholinergic agent in an amount sufficient to have a local antisecretory effect on the area treated, such amount being insufficient to cause systemic effects; and applying the transdermal delivery system to the pre-treated area. The delivery system of the present invention is comprised of a carrier means, a pharmaceutically active drug and an anticholinergic agent. With both the method and the delivery system, the anticholinergic agent is preferably a quaternary ammonium salt which is itself transdermally delivered to the area beneath the delivery system in an amount sufficient to suppress perspiration in that area. The suppression of perspiration prevents the formation of an aqueous interface between the skin and delivery system which might prevent drug delivery.

6 Claims, No Drawings

PHYSIOLOGICAL MEANS OF ENHANCING TRANSDERMAL DELIVERY OF DRUGS

This application is a continuation-in-part of application Ser. No. 659,919, filed Oct. 11, 1984 now abandoned.

FIELD OF THE INVENTION

The present invention relates to the field of transdermal delivery systems and to methods of enhancing the transdermal delivery of pharmaceutically active drugs from such systems. More specifically, the invention relates to such systems which include an anticholinergic agent in an amount sufficient to have a local antisecretory effect on skin, such an amount being insufficient to cause a systemic effect. The invention also relates to pre-treating the skin with anticholinergic agents so as to locally inhibit secretion from the skin and thereby eliminate the formation of an aqueous layer between any delivery system and the skin so as to enhance penetration of drugs from transdermal delivery systems.

BACKGROUND OF THE INVENTION

It is well known that many drugs if taken orally, are destroyed on the first past through the liver. It is also well known that when many drugs are taken orally, their rate of absorption into the body is not constant. In view of such difficulties, a number of different drug delivery systems have been developed. Recently, the use of transdermal delivery systems have met with increasing interest by researchers in the pharmaceutical drug delivery field.

U.S. Pat. No. 4,291,015 to Keith, et al. discloses the use of a polymeric diffusion matrix for the sustained release of pharmaceutically active drugs. The matrix is covered by a backing layer and applied to the skin where diffusion of the pharmaceutically active drug occurs and the drug is transdermally delivered to the patient. Although U.S. Pat. No. 4,291,015 discloses transdermal delivery of nitroglycerin, other drugs may be delivered by utilizing the same or a similar matrix, as disclosed in U.S. Pat. Nos. 4,294,820; 4,292,302; and 4,292,303.

U.S. Pat. No. 4,409,206 discloses the use of a different type of transdermal delivery system whereby the pharmaceutically active drug is dispersed within an adhesive (see also U.S. Pat. No. 4,390,520). In accordance with such systems, the pharmaceutically active drug is dispersed in a pressure-sensitive adhesive which is adhered to the skin. The drug then diffuses from the adhesive through the skin for delivery to the patient.

Other transdermal systems involve the use of a matrix which is in diffusional contact with a reservoir which contains the pharmaceutically active drug. The drug diffuses to the matrix and then to the skin and eventually to the patient. Still other compositions include an active ingredient in a salve or ointment which is applied to skin. The active ingredient diffuses from the salve to the skin and enters the body transdermally.

Each of the systems have various advantages and disadvantages with respect to the transdermally delivery of pharmaceutically active drugs. Certain systems may be useful in connection with one type of pharmaceutically active drug and not useful in connection with another. The ability to include one pharmaceutically active drug within a given system depends on various factors such as the compatibility of the drug with the system and the effects of the drugs on the system such as its ability to dissolve in the system.

Pharmaceutically active drugs for use in the present invention include transdermally deliverable physiologically or pharmacologically active substances for producing a localized or systemic effect in mammals, especially humans. The active drugs that can be used in the present invention are well known. See for example, U.S. Pat. No. 3,921,636 wherein one may find the following list of transdermally deliverable drugs: drugs acting on the central nervous system, such as hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and α-bromoisovaleryl urea and the like; hypnotics and sedative alcohols such as carbomal, naphthoxyethanol, methylparaphenol and the like; and hypnotics and sedative urethans, disulfanes and the like; psychic energizers such as isocarboxacid, nialamide, phenelzine, imipramine, tranylcypromine, pargylene and the like; tranquilizers such as chloropromazine, promazine, fluphenazine, reserpine, deserpidine, meprobamate, benzodiazepines such as chlordiazepoxide and the like; anticonvulsants such as primidone, diphenylhydantoin, ethotoin, pheneturide, ethosuximide and the like; muscle relaxants and antiparkinson agents such as mephenesin, methocarbomal, trihexylphenidyl, biperiden, levo-dopa, also known as L-dopa and 1-β-3-4-dihydroxyphenylalanine, and the like; analgesics such as morphine, codeine, meperidine, nalorphine and the like; anti-pyretics and anti-inflammatory agents such as aspirin, salicylamide, sodium salicylamide and the like; local anesthetics such as procaine, lidocaine, naepaine, piperocaine, tetracaine, dibucaine and the like; antispasmodics and antiulcer agents such as papaverine, prostaglandins such as $PGE_1$, $PGE_2$, $PGF_{1a}$, $PGF_{2a}$, PGA and the like; antimicrobials such as pencillin, tetracycline, oxytetracycline, chlorotetracycline, chloramphenicol, sulfonamides and the like; anti-malarials such as 4-aminoquinolines, 8-aminoquinolines and pyrimethamine; hormonal agents such as prednisolone, cortisone, cortisol and triamcinolone; androgenic steroids, for example methyltestosterone, fluoximesterone and the like; estrogenic steroids, for example, 17β-estradiol and ethinyl estradiol; progestational steroids, for example 17α-hydroxyprogesterone acetate, 19-nor-progesterone, norethindrone and the like; sympathomimetic drugs such as epinephrine, amphetamine, ephedrine, norepinephrine and the like; cardiovascular drugs, for example procainamide, amyl nitrate, nitroglycerin, dipyridamole, sodium nitrate, mannitol nitrate and the like; diuretics, for example, chlorothiazide, flumethiazide and the like; antiparastic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically, active agents. Also the drugs can be present as the pharmacologically acceptable derivatives, such as ethers, esters, amides, acetals, etc. that lend themselves to passage into the circulatory system.

As indicated above, the systems have various advantages, disadvantages, and degrees of usefulness in connection with different types of drugs. Without experimentation, it is often impossible to accurately predict the usefulness of any particular system with any particular pharmaceutically active drug. However, the present inventor has found that all the systems do have certain similarities and more importantly a common undesirable feature. More specifically, they all operate by transporting the pharmaceutically active drug to the skin for transdermal delivery. In order to accomplish this, the system must be placed in intimate contact with the skin. Since normal skin will perspire such will create an aqueous layer between the skin and the system. It is this aqueous layer which causes the common disadvantage.

Perspiration may well be increased beneath a transdermal delivery system and any perspiration beneath a delivery system causes an outflow of water and other water soluble body salts from the skin. This increased outflow increases the size of the aqueous layer and thus hinders the desired inflow of the pharmaceutically active drug through the skin. When the system remains in place for a substantial period of time (24 hours is common), the outflow of perspiration can build up a substantial aqueous layer between the delivery system and the skin. This impediment is especially great if the pharmaceutically active drug is insoluble with respect to the aqueous layer or if the drug is in any way incompatible with the aqueous layer or coagulates upon contact with it. The present invention is directed to elimination of the undesirable outflow of perspiration from the skin and the undesirable accumulation of that perspiration (aqueous layer formation) between the skin and the drug delivery system.

SUMMARY OF THE INVENTION

In its simplest form, the present invention involves the local application of an anticholinergic, preferably an anhidrotic agent, to the skin to prevent perspiration and thus indirectly enhance transdermal delivery of a pharmaceutically active, preferably non-anticholinergic, drug. Local application may be carried out by pre-treating an area of skin with an anticholinergic agent in an amount sufficient to have a local antisecretory effect on the area treated, such amount being insufficient to cause a systemic effect, and then applying a transdermal delivery system to the pre-treated area. Alternatively, the invention can be carried out by including the anticholinergic agent with the transdermal delivery system in such a manner that the anticholinergic agent can be delivered through the skin to prevent perspiration. The anticholinergic agent may be incorporated in a diffusion matrix, dispersed in a reservoir connected to such a matrix, included in a separate reservoir, dispersed in an ointment or connected in any other manner making it possible for the delivery of the anticholinergic agent through the skin to which the transdermal delivery system will be applied.

It is a primary object of the present invention to provide a physiological means of enhancing transdermal delivery of drugs.

Another object of the present invention is to deliver, to an area of skin, an anticholinergic agent in an amount sufficient to have a local antisecretory effect on the area of skin, such amount being insufficient to cause a systemic effect.

Yet another object of the invention is to provide a method of enhancing the transdermal delivery of a pharmaceutically active drug from a transdermal delivery system by pre-treating an area of skin with an anticholinergic agent and applying a transdermal delivery system to the pre-treated area.

Another object of the invention is to provide a transdermal delivery system capable of providing a desirable flow interface between the delivery system and skin surface, comprising a carrier means, a pharmaceutically active drug and an anticholinergic agent present in an amount sufficient to have a local antisecretory effect on the skin below the system, such amount being insufficient to cause a systemic effect.

Yet another object of the invention is to provide such systems and means whereby the anticholinergic agents are quaternary ammonium salts of such agents.

These and other objects of the invention will become apparent to those skilled in the art upon reading this disclosure.

DETAILED DESCRIPTION OF THE INVENTION

There are a number of known chemical compounds which are known as "penetration enhancers". Such compounds interact in some manner with a pharmaceutically active drug and enhence the penetration of that drug through the skin. Perhaps the most famous of such penetration enhancers is "DMSO (dimethyl sulfoxide)". However, DMSO has not received FDA approval for use on humans. Another well known penetration enhancer is AZONE, see U.S. Pat. Nos. 3,989,816, 4,311,481 and 4,316,893 as well as the corresponding foreign patents.

Such known penetration enhancers have a physical and/or chemical means of enhancing the penetration of the pharmaceutically active drug. Such compounds may themselves be easily transported through the skin and thus enhance the skin permeability, allowing transport of the pharmaceutically active drugs at significantly higher flux. The enhancers may also have the effect of neutralizing molecular charges on the pharmaceutically active drugs, thus making them more susceptible to penetration of the skin.

Although such penetration enhancers are useful and might even be used in combination with the present invention, they do not cause the same physiological effect on the skin as does the present invention.

After making a thorough study of the transdermal delivery systems, the present inventor found that the transdermal delivery of pharmaceutically active drugs through the skin could be hindered by the outflow of perspiration from the skin and subsequent formation of an aqueous layer over the skin. The present inventor noted that transdermal delivery systems were normally worn for a long period of time, generally about twenty-four hours (24). When delivery systems are worn for such extended periods of time, substantial perspiration from the skin is very likely to build up between the outer layer of the skin and the contact layer of the transdermal delivery system. The aqueous layer of perspiration thus formed between the delivery system and the skin interrupts the desired interface between the skin and the delivery system having an undesirable effect on the delivery of drugs from the system.

The present inventor noted that the above referred to problem could at times, be at least partially remedied by including additional pharmaceutically active drug into the delivery system. Such a solution is, of course, only possible where additional drug may be incorporated into the system without having undesirable effects. Such effects may take place where the pharmaceutically active drug acts as a solvent with respect to the system causing dissolution of the system. Further, even in situations where additional drug can be incorporated into the delivery system the problem is not completely solved in that individuals vary with respect to the amount they perspire and even a given individual may generate greatly different amounts of perspiration depending on the temperature, humidity and activity of the individual.

Due to individual differences in the amount of perspiration generated as well as the amount of perspiration a particular individual might be generating at any particular time, the present inventor found that the rate of drug delivery from a transdermal drug delivery system could vary. Such variance in the amount of drug delivered is, of course, undesirable in that the physician would prefer to prescribe a delivery system with which an accurate determination could be made with respect to the rate of delivery of the pharmaceutically active drug. The realization of the problems caused by perspiration when utilizing the transdermal delivery systems precipitated the discovery of the present invention by the present inventor.

After determining that perspiration from the skin causes problems with transdermal delivery systems, the present inventor determined that preventing that perspiration would solve the problems related thereto. According, an examination of various compounds utilized for preventing perspiration was made. Commercially available antiperspirants normally sold in the form of roll-ons and sprays are effective in preventing perspiration. Such compositions are normally aluminum based and prevent perspiration by a physical blocking means, i.e. the compounds actually clog the canals through which the perspiration passes. Since such compounds actually operate by clogging the passage ways out of the skin, the use of such compounds might not be desirable with respect to increasing the inflow of a pharmaceutically active drug through the skin. Although use of such compounds might avoid the formation of an aqueous layer between the skin and the transdermal delivery device, such compounds might themselves create barriers for the inflow of pharmaceutically active drugs through the skin.

The present inventor has done substantial work with anticholinergic compounds as shown in U.K. Patent No. 2,010,270 which discloses soft anticholinergic agents exhibiting antisecretory activity. Accordingly, the present inventor carried out experiments in order to determine if the use of such anticholinergic compounds would inhibit the inflow of pharmaceutically active drugs from a transdermal delivery device and found that the inflow of drugs was not inhibited. Knowing that such anticholinergic drugs prevented the outflow of perspiration and thus the formation of any aqueous layer, it was deduced that the effects of anticholingeric agents would increase the inflow of pharmaceutically active drugs through the skin.

Anticholinergic drugs affect the nervous system. The systemic effect on the nervous system is undesirable in connection with the present invention. Accordingly, the topical application of a small amount of anticholinergic agents to the skin is all that is necessary and desirable in order to obtain the results of the invention.

The normal working physiology of a human being provides a neurohumoral transmitter substance which provokes a stimulant action. For example, such a substance can evoke a stimulant action with respect to secretion glands within the skin and cause perspiration. However, within the normal physiology with a human, there is no comparable substance which provides an inhibitory action. There are, however, synthetic and plant-produced compounds that provide such inhibitory action. Such compounds act by blocking synaptic transmission in either the sympathetic or parasympathetic innervations. The present inventor noted that the blocking action of these inhibitors is usually quite specific to its locus. The use of such agents can cause blocking at the ganglionic nerve terminations (synapses) in either the sympathetic or parasympathetic ganglia, at the post ganglionic nerve terminations of either system (nerve-muscle junction blocking agent).

A chart is set forth below showing the various sites of blocking action of anticholinergic agents.

| SITE OF BLOCKING ACTION | NEURO-HUMORAL TRANSMITTER SUBSTANCE | TYPE OF BLOCKING ACTION | EXAMPLE OF DRUG |
|---|---|---|---|
| AUTONOMIC BLOCKING AGENTS | | | |
| Sympathetic Ganglion | Acetylcholine | Anti-cholinergic | Hexamethonium |
| Postganglionic Synapse | Norepinephrine (and epinephrine) | Anti-adrenergic | Dibenamine |
| Parasympathetic Ganglion | Acetylcholine | Anti-cholinergic | Hexamethonium |
| Postganglionic Synapse | Acetylcholine | Anti-cholinergic | Atropine |
| Voluntary* Neuromuscular Junction | Acetylcholine | Anti-cholinergic | Curare |

*Included as a matter of convenience and because of certain similarities with the ganglionic blocking agents. These drugs are not autonomic blocking agents.

A number of different therapeutic actions can be obtained by the use of anticholinergic agents. The effect of such agents include the following:

1. Mydriatic effect (dilation of pupil of the eye) and cycloplegia (a paralysis of the ciliary structure of the eye, resulting in a paralysis of accommodation for near vision).

2. Antipasmodic effect (lowered tone and motility of the gastrointestinal tract and the genitourinary tract).

3. Antisecretory effect (reduced salivation (antisialogogue), reduced perspiration (anhidrotic) and reduced acid and gastric secretion).

As indicated above the anticholinergic agents have a substantial number of different effects on the human body. Accordingly, it is undesirable unless absolutely necessary to prescribe such agents in an amount such that they have a systemic effect. Therefore, it would be undesirable to prescribe such anticholinergic agents for oral usage simply to prevent perspiration which would then indirectly facilitate transdermal delivery of a drug from a transdermal delivery system. The mechanism of action of such drugs is obscure, but such drugs do affect a central mechanism. However, in order to affect a central mechanism and have a systemic effect the compounds must past the blood-brain barrier. Upon research, it was found that tertiary amines of such anticholinergic compounds can pass this blood-brain barrier but that quaternary ammonium compounds could not.

Tertiary amines of certain anticholinergic compounds have been shown to increase the brain acetylcholine levels in rats up to 40%. This increase coincides roughly with the onset of tremors similar to those observed in parkinsonism. The mechanism of acetylcholine increase in rats in uncertain but it has been shown not to be due to acetylcholinesterase inhibition or to activation to acetylase. However, the tremors are stopped effectively by administration of the tertiary amine type anticholinergic but not by the quaternary ammonium compounds.

Although any of the anticholinergic compounds can prevent secretion and thus aide in the transdermal delivery of a drug from a transdermal delivery system, due to the undesirable side effects of some of these compounds, the present inventor determined that it would be most desirable to utilize quaternary ammonium salts of known anticholinergic compounds, and has further determined that the topical application of such compounds in small amounts would be most desirable in terms of obtaining the desired effects of the present invention and avoiding undesirable side effects.

The following fare specific examples of quaternary ammonium salts of anticholinergic compounds preferably used in connection with the present invention.

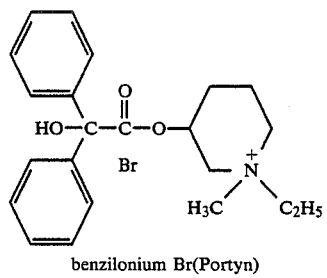

benzilonium Br(Portyn)

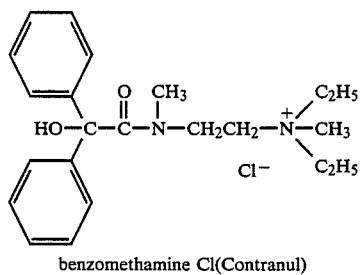

benzomethamine Cl(Contranul)

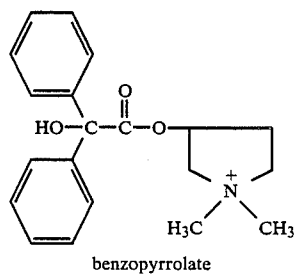

benzopyrrolate

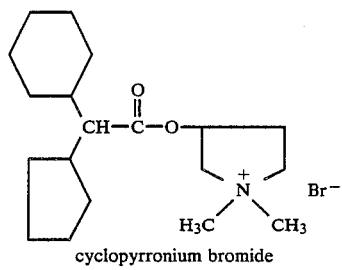

cyclopyrronium bromide

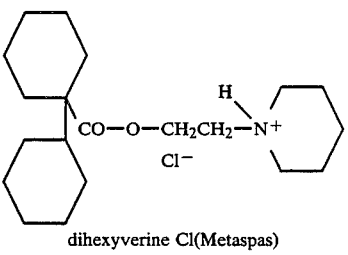

dihexyverine Cl(Metaspas)

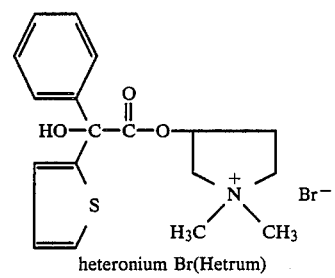

heteronium Br(Hetrum)

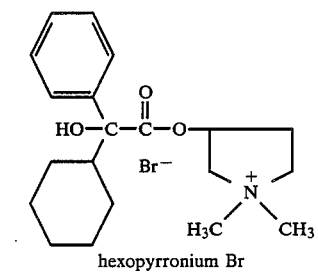

hexopyrronium Br

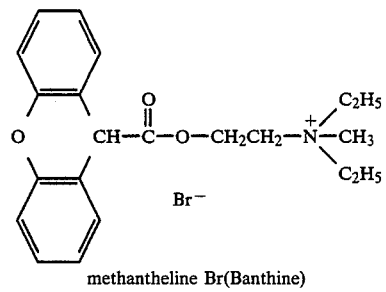

methantheline Br(Banthine)

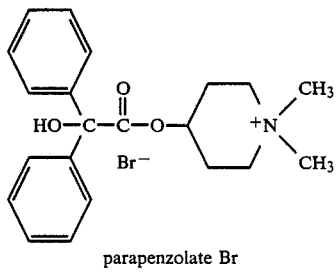

parapenzolate Br

-continued

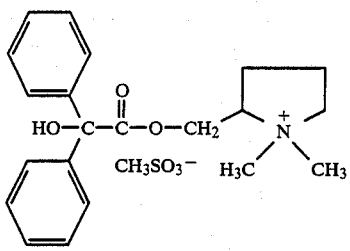

poldine mesylate(Nacton)

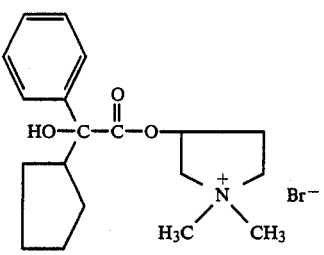

GLYCOPYRROLATE METHOBROMIDE(Robinul)

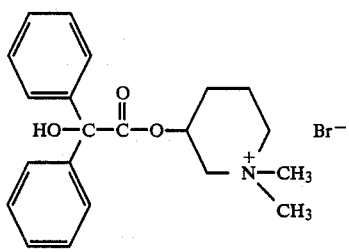

MEPENZOLATE METHYLBROMIDE(Cantil)

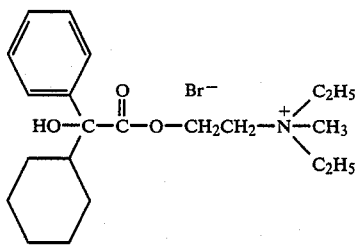

OXYPHENONIUM BROMIDE(Antrenyl)

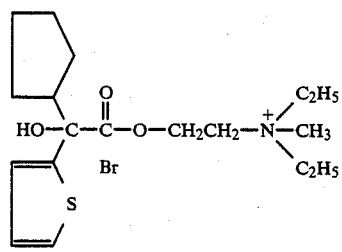

PENTHIENATE BROMIDE(Monodral)

-continued

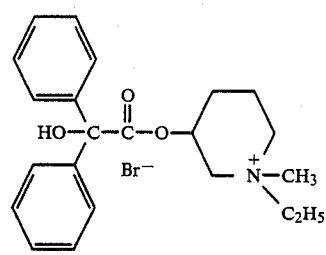

PIPENZOLATE METHYLBROMIDE(Piptal)

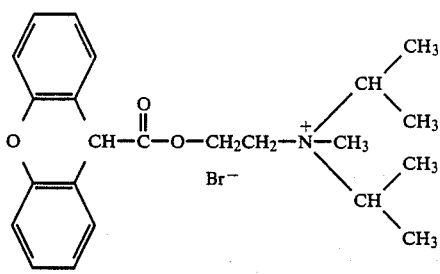

PROPANTHELINE BROMIDE(Pro-Banthine)

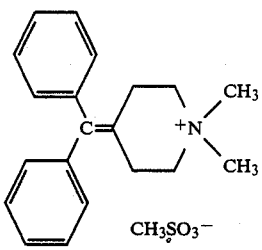

DIPHEMANIL METHYLSULFATE(Prantal)

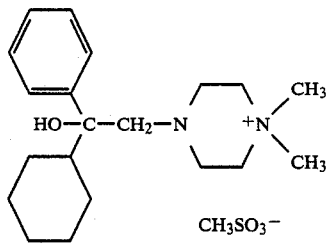

HEXOCYCLIUM METHYLSULFATE(Tral)

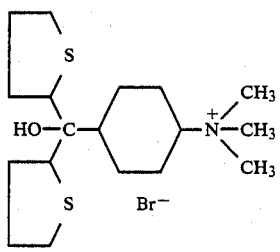

THIHEXINOL METHYLBROMIDE(Entoquel)

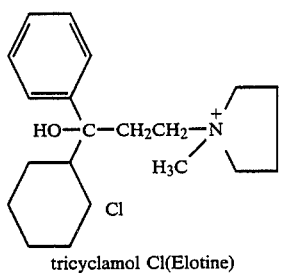
tricyclamol Cl(Elotine)

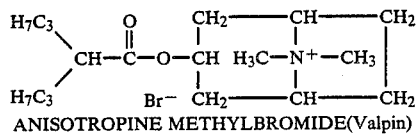
ANISOTROPINE METHYLBROMIDE(Valpin)

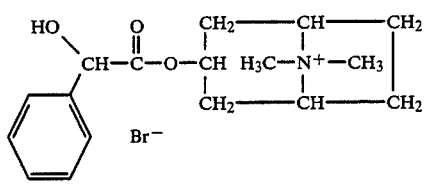
HOMATROPINE METHYLBROMIDE(Novatrin, and others)

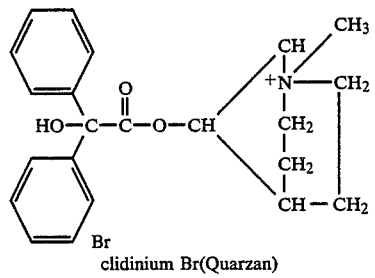
clidinium Br(Quarzan)

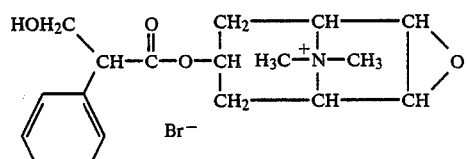
METHSCOPOLAMINE BROMIDE(Pamine, and others)

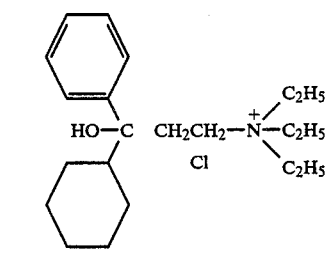
TRIDIHEXETHYL CHLORIDE(Pathilon)

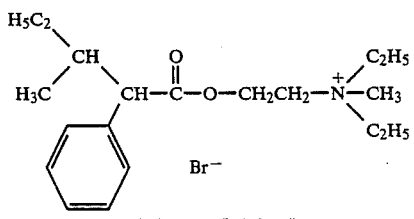
valethamate Br(Murel)

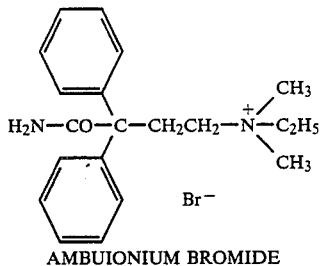
AMBUIONIUM BROMIDE

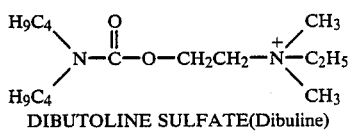
DIBUTOLINE SULFATE(Dibuline)

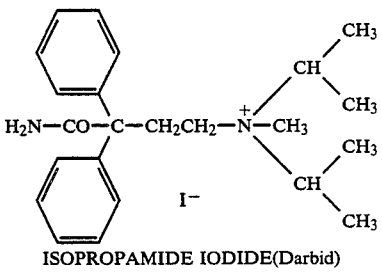
ISOPROPAMIDE IODIDE(Darbid)

In order to describe some aspects of how the present invention works, the mechanism of a specific compound will be discussed. It is generally agreed that the activity of atropine-related anticholinergics is a competitive one with acetylcholine. Accordingly, the cholinomimetic agent (i.e. acetylcholine) possesses both affinity and intrinsic activity and can be bound to the receptor site and elicit the characteristic mimetic response. The anticholinergic agent, on the other hand, has the necessary affinity to bind firmly to the receptor but is unable to bring about an effective response, i.e., it has no intrinsic activity. The blocking agent, in sufficient concentration effectively competes for the receptor sites and prevents acetylcholine from binding thereon, thus preventing nerve activity.

With the present invention, the anticholinergic molecules have a primary point of attachment to cholinergic sites through the so called cationic head, i.e., the positively charged nitrogen present on the quaternary ammonium salts preferably used in connection with the present invention. Accordingly, the quarternary ammonium salts of anticholinergic agents preferred for use in the present invention actually penetrate the skin and attach themselves on receptor sites. This prevents other agents which cause intrinsic activity from attaching to that site. When topically applied to the skin the anticholinergic agent physiologically interrupts the normal course of events and prevents perspiration. Unlike antiperspirants which are sold commerically, the anticholinergic agents of the present invention do not cause a physical blocking of any channels from which perspiration flows. The compounds of the present invention simply prevent secretion before it starts.

In order to determine if the anticholinergic agents of the present invention had any negative effect on the delivery of pharmaceutically active drugs from a transdermal delivery system, the inventor tested the invention on hairless mice. Knowing that hairless mice do not perspire, an anticholinergic agent was topically applied to an area of skin on hairless mice and a transdermal delivery system was then applied over the area to which the anticholinergic agent was applied. An identical transdermal delivery device was applied to a different mouse to which no anticholinergic agent had been applied. The inventor found that both mice received the same amount of pharmaceutically active drug from the transdermal delivery system. Accordingly, it was deduced that the use of the anticholinergic agent had no effect on the transdermal delivery or the drug in an in vivo environment where no perspiration occurs. The present inventor then further deduced that the topical application of anticholinergic agents to human skin (where perspiration does occur) would facilitate the delivery of drugs from transdermal delivery systems in that such agents clearly do effectively prevent perspiration.

As indicated above, any type of anticholinergic agent can be utilized in connection with the present invention. However, the present inventor believes that quaternary ammonium compounds as indicated above and those disclosed within U.K. Patent No. 2,010,270 are preferably used in connection with the present invention. Compounds disclosed therein are of the general formula I or II below:

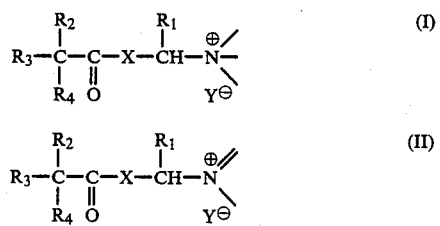

wherein

represents a tertiary amine,

represents an unsaturated amine and $R_2$, $R_3$ and $R_4$ which may be the same or different provided that at least two of the groups represented by $R_2$, $R_3$ and $R_4$ must be other than a hydrogen atom, and provided that $R_2$, $R_3$ and $R_4$ together must contain at least 5 carbon atoms) each represents a hydrogen atom, a straight or branched-chain alkyl or alkoxy group having from 1 to 8 carbon atoms, a cycloalkyl or cycloalkenyl group having up to 8 carbon atoms, an alkoxyalkyl, acyloxyalkyl, haloalkyl or carboxyalkyl group each having up to 8 carbon atoms, an alkenylphenyl group having up to 8 carbon atoms in the alkenyl moiety, an aryl group (unsubstituted or substituted by a halogen atom, an alkoxy group having from 1 to 4 carbon atoms, an acyloxy group, a nitro group, a carboxyl group or a carboethoxy group), a $CH_2OH$ group, a —$CHOCOR_1$ group (wherein $R_1$ is as defined below or a —$CH_2ONO_2$ grup), an —OH group, a halogen atom or a —$OCOR_1$ group (wherein $R_1$ is as defined below) or a —$ONO_2$ group; or $R_2$ is as hereinbefore defined and $R_3$, $R_4$ and the carbon atom to which they are attached form a cyclo-alkyl group having up to 8 carbon atoms; or the groups represented by $R_2$, $R_3$ and $R_4$ and the carbon atom to which they are attached form a fused polycarbocyclic ring or a polyheterocyclic ring; and $R_1$ represents any group which is capable of being represented by $R_2$, $R_3$ or $R_4$ as hereinbefore defined; —X— represents —O— or —S—; and Y represents a halogen atom or any other organic or inorganic anion.

In the above formulae, reference to "aryl" denotes a phenyl or naphthal group; reference to "halo" and "halogen" in each occurrence, denotes any suitable member of the halogen series, for example, chlorine, bromine or iodine; and reference to "acyl" in the expression "acyloxyalkyl" and "acyloxy" denotes any convenient carboacyl group, such as a formyl group, an acetyl group, a propionyl group, a benzoyl group, etc. It is further noted that the term "substituted" when applied to the aryl group refers to the fact that the aryl function may be substituted with any one or more of those substituents specifically defined herein. With regard to substituent "Y", when this substituent is other than halogen, methanesulfonate, fluorosulphate or tosylate are preferred.

Finally, with respect to the expression "unsaturated amine", this expression is intended to include N-heterocyclic unsaturated systems having 3–10 members in the ring, and substituted derivative thereof where the unsaturation corresponds to the maximum number of non-cumulative double bonds, provided that the nitrogen atom contains no hydrogen atom as a substituent.

The anticholinergic agents which are quaternary ammonium salts as shown above and disclosed in U.K. Patent No. 2,010,270 are believed to be more useful in connection with the present invention in that they are "soft" in nature, i.e., these agents exhibit substantial anticholinergic antisecretory activity, while having low toxicity following therapeutic application. They do not pass the "brain barrier." Other anticholinergic agents exhibit substantial anticholinergic antisecretory activity, but in addition these compounds give rise to a number of toxic side effects such as dizziness, blurred vision and dry mouth.

In order to obtain the effects of the present invention small amounts of the anticholinergic agents are utilized. For example, a useful composition can be prepared using anisotropine methylbromide (Valpin) as the anticholinergic agent (see Merck Index Tenth Edition, Entry Number 693) This agent is very soluble in alcohols. Accordingly, 20 milligrams can be dissolved in 25 milliliters of ethanol and 200 microliters of the solution can be applied to about five or six square centimeters of skin surface. This amount will prevent perspiration from that area for a period sufficient for the purposes of the present invention, i.e. about twenty-four (24) hours or more.

In order to make use of the present invention the anticholinergic agents can be dissolved in any suitable dermatologically acceptable solvent and applied by any known means to the surface area of skin to which a transdermal delivery device is to be applied. Alternatively, the agents may be included in any transdermal system. The anticholinergic agents of the invention are themselves capable of migrating transdermally. Accordingly, they can be merely placed on the skin, rubbed into the skin, sprayed on the skin or placed in contact with the skin as part of the transdermal delivery system. In order to obtain a cleansing effect which is an additional benefit when utilizing a transdermal delivery device, the anticholinergic agent can be placed onto an applicator such as a cotton swab or cloth which has the agent thereon dissolved in alcohol. The applicator having the agent dissolved thereon is then rubbed on the area of skin to which the device is to be applied. The alcohol has a cleansing antiseptic effect on the area and the anticholingeric compound is allowed to permeate the skin. The transdermal delivery device is then applied over the area which has been pre-treated. An agent known to enhance skin penetration might also be included on the applicator.

In addition to pre-treating an area of skin with an anticholinergic agent, it is possible to utilize the present invention by incorporating the anticholinergic agent into the transdermal delivery system. The penetration enhancers present in such a system might also enhance penetration of the anticholinergic agent. The agents of the invention can be incorporated into a matrix system, included into a reservoir with a pharmaceutically active drug, dispersed in an adhesive layer or ointment or otherwise included in connection with the system in some manner so that the agent may be delivered through the surface of the skin.

As indicated above, a large number of different types of pharmaceutically active drugs are now being considered for use in transdermal delivery systems. Further, as indicated above, a large number of different types of systems are utilized for delivering these drugs. Since the present invention can conceivably be used in connection with all types of transdermal delivery systems, the present inventor conceived of a preferred embodiment of his invention whereby the invention could be utilized in connection such systems without substantial modification More specifically, anticholinergic agents of the invention could be absorbed on an applicator such as a piece of cotton cloth or other suitable soft pliable material, preferably in an alcohol type solvent. The solvent must be dermatologically acceptable and preferably have antiseptic properties. The applicator having the anticholinergic agent absorbed thereon is then incorporated into a separate packet or reservoir which is connected to the transdermal delivery system. This packet or reservoir can be opened prior to the application of the transdermal delivery system. Upon opening, the applicator is removed and the area of skin to which the system is to be applied is pre-treated by rubbing the area of skin with the applicator, thus cleansing the skin and allowing for transdermal delivery of the anticholinergic composition. After pre-treatment, the transdermal delivery device is applied to the pre-treated area. Delivery of the pharmaceutically active drug from the transdermal delivery system should be facilitated by the present invention in that perspiration from the pre-treated area of skin will be interrupted thus preventing the outflow of water from that area of skin and preventing the build up of any aqueous layer between the surface of the skin and the transdermal delivery system.

The present invention has been disclosed and described herein in which is believed to be its more preferred embodiments. However, upon reading this disclosure those skilled in the art will recognize modifications and variations thereof which are intended to be within the scope of the present invention.

I claim:

1. An improved transdermal delivery system comprising:
   a pharmaceutically active, non-anticholinergic, transdermally deliverable drug;
   an anhidrotic agent; and
   a transdermal delivery system means for applying said active drug and said anhidrotic agent to an area of the skin;
   wherein said anhidrotic agent is a quaternary ammonium salt, and is present in an amount sufficient to have a local anhidrotic effect but insufficient to cause a systemic anhidrotic effect, whereby the transdermal delivery of said active drug is enhanced.

2. A transdermal delivery system of claim 1, wherein the anhidrotic agent is an antisecretory anticholinergic agent.

3. The transdermal delivery system of claim 1 wherein the anhidrotic agent is mixed with the pharmaceutically active non-anticholinergic drug.

4. The transdermal delivery system of claim 1 wherein the anhidrotic agent is provided separately from the pharmaceutically active non-anticholinergic drug.

5. A transermal delivery system of claim 1 wherein the transdermal delivery system means is a matrix system, a reservoir system or an adhesive system.

6. The transdermal delivery system of claim 2 wherein the anticholinergic antiperspirant agent is selected from benzilonium bromide, benzomethamine chloride, benzopyrrolate, cyclopyrronium bromide, dihexyverine chloride, heteronium bromide, hexopyrronium bromide, methantheline bromide, parapenzolate bromide, poldine mesylate, glycopyrrolate, mepenzolate methylbromide, oxyphenonium bromide, penthienate bromide, pipenzolate methylbromide, propantheline bromide, diphemanil methylsulfate, hexocyclium methylsulfate, thihexinol methylbromide, tricyclamol, anisotropine, methylbromide, homatropine methylbromide, clidinium bromide, methscopolamine bromide, tridihexethyl choride, valethamate bromide, ambutonium bromide, dibutoline sulfate, isopropamide iodide, and compounds of the formulae

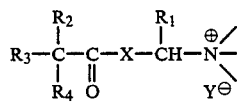

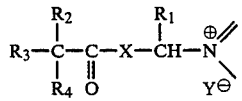

wherein

represents a tertiary amine, $$N\diagdown^{\diagup\diagup}$$

represents an unsaturated amine and $R_2$, $R_3$ and $R_4$ (which may be the same or different provided that at least two of the groups represented by $R_2$, $R_3$ and $R_4$ must be other than a hydrogen atom, and provided that $R_2$, $R_3$ and $R_4$ together must contain at least 5 carbon atoms) each represents a hydrogen atom, a straight or branched-chain alkyl or alkoxy group having from 1 to 8 carbon atoms, a cycloalkyl or cycloalkenyl group having up to 8 carbon atoms, an alkoxyalkyl, acyloxyalkyl, haloalkyl or carboxyalkyl group each having up to 8 carbon atoms, an alkenylphenyl group having up to 8 carbon atoms in the alkenyl moiety, an aryl group (unsubstituted or substituted by a halogen atom, an alkoxy group having from 1 to 4 carbon atoms, an acyloxy group, a nitro group, a carboxyl group or a carboethoxy group), a $CH_2OH$ group, a $-CHOCOR_1$ group (wherein $R_1$ is as defined below or a $-CH_2ONO_2$ group), an $-OH$ group, a halogen atom or a $-OCOR_1$ group (wherein $R_1$ is as defined below) or a $-ONO_2$ group; or R is as hereinbefore defined and $R_3$, $R_4$ and the carbon atom to which they are attached form a cyclo-alkyl group having up to 8 carbon atoms; or the groups represented by $R_2$, $R_3$ and $R_4$ and the carbon atom to which they are attached form a fused polycarbocyclic ring or a polyheterocyclic ring; and $R_1$ represents any group which is capable of being represented by $R_2$, $R_3$ or $R_4$ as hereinbefore defined; $-X-$ represents $-O-$ or $-S-$; and Y represents a halogen atom or any other organic or inorganic anion.

* * * * *